United States Patent
Han et al.

(10) Patent No.: US 11,371,934 B2
(45) Date of Patent: Jun. 28, 2022

(54) METHOD FOR CORRECTING LIGHT INTENSITY MEASUREMENT VALUE AND CONCENTRATION MEASUREMENT DEVICE IN WHICH REFERENCE VALUE IS MEASURED AT TIME GATE FIXED OPTICAL LENGTH

(71) Applicants: TIANJIN UNIVERSITY, Tianjin (CN); Tianjin Sunrise Technologies Development Co., Ltd., Tianjin (CN)

(72) Inventors: Guang Han, Tianjin (CN); Jun He, Tianjin (CN); Kexin Xu, Tianjin (CN)

(73) Assignees: TIANJIN UNIVERSITY, Tianjin (CN); TIANJIN SUNRISE TECHNOLOGIES DEVELOPMENT CO., LTD., Tianjin (CN)

( * ) Notice: Subject to any disclaimer, the term of this patent is extended or adjusted under 35 U.S.C. 154(b) by 11 days.

(21) Appl. No.: 17/050,530

(22) PCT Filed: Jun. 28, 2019

(86) PCT No.: PCT/CN2019/093776
§ 371 (c)(1),
(2) Date: Oct. 26, 2020

(87) PCT Pub. No.: WO2019/206345
PCT Pub. Date: Oct. 31, 2019

(65) Prior Publication Data
US 2021/0131956 A1 May 6, 2021

(30) Foreign Application Priority Data
Apr. 28, 2018 (CN) .......................... 201810409248.1

(51) Int. Cl.
*G01N 21/359* (2014.01)
*A61B 5/00* (2006.01)
(Continued)

(52) U.S. Cl.
CPC ......... *G01N 21/359* (2013.01); *A61B 5/0075* (2013.01); *G01J 3/4412* (2013.01);
(Continued)

(58) Field of Classification Search
CPC ...... G01N 21/359; G01N 21/17; G01N 21/25; G01N 21/35; G01N 21/49; G01N 33/66; A61B 5/0075; G01J 3/4412
See application file for complete search history.

(56) References Cited

U.S. PATENT DOCUMENTS 5,962,852 A * 10/1999 Knuettel ............ A61B 5/1455
250/339.11
8,346,329 B2   1/2013 Xu et al.
(Continued)

FOREIGN PATENT DOCUMENTS

CN        1699973 A    11/2005
CN      101002683 A     7/2007
(Continued)

OTHER PUBLICATIONS

International Search Report and Written Opinion for International Application No. PCT/CN2019/093776, dated Sep. 20, 2019, 6 pages.
(Continued)

*Primary Examiner* — Dominic J Bologna
(74) *Attorney, Agent, or Firm* — Westman, Champlin & Koehler, P.A.

(57) ABSTRACT

The present disclosure provides a method for correcting a light intensity measurement value is provided. The method includes: emitting detection light into a measured object; measuring a light intensity measurement value at a measurement position, and measuring light intensity of photons at a benchmark position as a light intensity reference value. A sensitivity of the light intensity of photons to a concentration change of a specific substance in the measured object is less than or equal to a preset threshold, and a change rate of the light intensity at the measurement position with a concentration of the specific substance in the measured object is greater than a change rate of the light intensity at the benchmark position with the concentration of the specific substance; correcting the light intensity measurement value by using the light intensity reference value. The present disclosure further provides a concentration measurement device.

16 Claims, 8 Drawing Sheets

(51) Int. Cl.
*G01J 3/44* (2006.01)
*G01N 21/49* (2006.01)
*G01N 33/66* (2006.01)
*G01N 21/17* (2006.01)
*G01N 21/25* (2006.01)
*G01N 21/35* (2014.01)

(52) U.S. Cl.
CPC ............ *G01N 21/17* (2013.01); *G01N 21/25* (2013.01); *G01N 21/35* (2013.01); *G01N 21/49* (2013.01); *G01N 33/66* (2013.01)

(56) References Cited

U.S. PATENT DOCUMENTS

| | | | |
|---|---|---|---|
| 8,996,338 B2 | 3/2015 | Xu et al. | |
| 10,054,594 B2 | 8/2018 | Xu et al. | |
| 2008/0171925 A1 | 7/2008 | Xu et al. | |
| 2011/0131021 A1* | 6/2011 | Xu | G01N 21/359 703/2 |
| 2015/0119661 A1* | 4/2015 | Gilbert | A61B 5/14539 600/316 |
| 2015/0346090 A1* | 12/2015 | Xu | G01N 21/27 356/341 |
| 2016/0091496 A1* | 3/2016 | Xu | A61B 5/1455 356/436 |

FOREIGN PATENT DOCUMENTS

| | | |
|---|---|---|
| CN | 101292875 A | 10/2008 |
| CN | 105510238 A | 4/2016 |

OTHER PUBLICATIONS

First Office Action, including Search Report, for Chinese Patent Application No. 201810409248.1, dated Jul. 5, 2021, 16 pages.

He Jun et al., "Effect of diffuse reflection path-length of near-infrared on sensitivity of glucose concentration detection", Infrared and Laser Engineering, vol. 45, No. S1, DOI: 10.3788/IRLA201645. S104006, May 2016.

Guang Han et al., "Floating reference position -based correction method for near-infrared spectroscopy in long-term glucose concentration monitoring", Journal of Biomedical Optics, vol. 22(7) DOI: 10.1117/1.JBO.22.7.077001, Jul. 2017.

* cited by examiner

METHOD FOR CORRECTING LIGHT INTENSITY MEASUREMENT VALUE AND CONCENTRATION MEASUREMENT DEVICE IN WHICH REFERENCE VALUE IS MEASURED AT TIME GATE FIXED OPTICAL LENGTH

CROSS-REFERENCE TO RELATED APPLICATION

This application is a Section 371 National Stage application of International Application No. PCT/CN2019/093776, filed on 28 Jun. 2019, which published as WO 2019/206345 A1 on 31 Oct. 2019, which claims priority to Chinese Patent Application No. 201810409248.1, entitled "method and device for measuring concentration in which reference value is measured at time gate fixed optical length", filed on Apr. 28, 2018 in China National Intellectual Property Administration, the disclosures of which are incorporated herein by reference in their entireties.

TECHNICAL FIELD

The present disclosure relates to the field of spectral detection technology, and in particular, to a method for correcting a light intensity measurement value and a concentration measurement device in which a reference value is measured at a time gate fixed optical length.

BACKGROUND

Near-infrared spectroscopy technology has been widely applied to detect concentrations of substance components in many fields such as food or drug detection, air pollution detection, and water quality monitoring. The clinical application of near-infrared spectroscopy is also one of the current research hotpots, especially near-infrared non-invasive blood glucose detection. The near-infrared non-invasive blood glucose detection can not only realize timely, safe and painless self-monitoring of blood glucose concentration, but also does not require consumables, so that it can greatly reduce detection costs and has a very high clinical application value.

Based on results and experience of various research groups at home and abroad, the current bottleneck restricting the accuracy and correctness of non-invasive human blood glucose concentration measurement is not due to the limitation of the signal-to-noise ratio of instrument hardware, but background change in the measurement process. How to eliminate an influence of background change and extract weak blood glucose change information from complex background change is a prerequisite for clinical application of non-invasive detection of human blood glucose concentration. Most of components in the blood, such as water, fat, protein, etc., have absorption in the near-infrared range, spectral peaks overlap with one another, factors such as biological activities and mood fluctuations of the organism and environmental influences will directly or indirectly affect the effective extraction of blood composition information, there are many and complex components in the blood and there are many and complex physiological factors, thus it is difficult to monitor the human blood glucose concentration in real time or measure it quantitatively at the current level of scientific research.

SUMMARY

In an aspect, the present disclosure provides a method for correcting a light intensity measurement value, wherein the method comprises:

emitting detection light into a measured object;

determining a benchmark position, a change rate of light intensity measured at the benchmark position with a concentration of a specific substance in the measured object being less than or equal to a preset threshold;

using the light intensity measured at the benchmark position as a light intensity reference value;

measuring a light intensity measurement value at a measurement position, wherein a change rate of the light intensity measured at the measurement position with the concentration of the specific substance in the measured object is greater than the change rate of the light intensity measured at the benchmark position with the concentration of the specific substance in the measured object; and correcting the light intensity measurement value by using the light intensity reference value.

Optionally, the method further comprises: utilizing a time gate device to control an optical detector to measure light intensity of photons of a specific optical length at the benchmark position.

Optionally, the benchmark position is a positional point or a positional area.

Optionally, the step of utilizing the time gate device to control the optical detector to measure light intensity of photons of the specific optical length at the benchmark position comprises: under different concentrations of the specific substance, by controlling the time when a light source for emitting the detection light is turned on and the time when the light source is turned off and controlling the time when the optical detector is turned on and the time when the optical detector is turned off by the time gate device, measuring light intensity of photons of different optical lengths at the benchmark position; determining the specific optical length of the photons, the change rate of the light intensity of the photons of the specific optical length with the concentration of the specific substance in the measured object being less than or equal to the preset threshold; and measuring the light intensity of the photons of the specific optical length at the benchmark position.

Optionally, the step of using the light intensity measured at the benchmark position as the light intensity reference value comprises: using the light intensity of the photons of the specific optical length measured at the benchmark position as the light intensity reference value.

Optionally, the change rate of the light intensity of the photons of the specific optical length with the concentration of the specific substance in the measured object is substantially equal to zero.

Optionally, in response to that the benchmark position is the positional point, a probe of the optical detector is disposed at the positional point; in response to that the benchmark position is the positional area, photons in the positional area are converged to the probe by using a light-converging method.

Optionally, in response to that the benchmark position is the positional point, the photons of the specific optical length are collected at the positional point by a probe of the optical detector; in response to that the benchmark position is the positional area, a lens is provided at the positional area to focus the photons in the positional area onto the probe.

Optionally, the benchmark position is a position where the change rate of the light intensity with the concentration of the specific substance in the measured object is the smallest among multiple positions that are at different distances from a light source in the measured object, and the measurement position is a position where the change rate of the light intensity with the concentration of the specific substance in the measured object is the largest among the multiple positions.

Optionally, the step of correcting the light intensity measurement value by using the light intensity reference value comprises: using light intensity of photons of all optical lengths measured at the benchmark position as the light intensity reference value; using the light intensity of the photons of the specific optical length measured at the benchmark position as a benchmark light intensity reference value; and correcting the light intensity measurement value by using the benchmark light intensity reference value, the light intensity reference value and the light intensity measurement value.

In another aspect, the present disclosure further provides a concentration measurement device, wherein the device comprises: a light source configured to emit detection light into a measured object; an optical detector configured to measure light intensity at at least one position in the measured object; and a processor which is in communication with the light source and the optical detector, wherein the processor is configured to: determine a benchmark position, a change rate of light intensity measured at the benchmark position with a concentration of a specific substance in the measured object being less than or equal to a preset threshold; use the light intensity measured at the benchmark position as a light intensity reference value; measure a light intensity measurement value at a measurement position, wherein a change rate of the light intensity measured at the measurement position with the concentration of the specific substance in the measured object is greater than the change rate of the light intensity measured at the benchmark position with the concentration of the specific substance in the measured object; and correct the light intensity measurement value by using the light intensity reference value.

Optionally, the device further comprises: an incident optical fiber, through which the detection light emitted from the light source is transmitted into the measured object; and an optical fiber probe, through which the optical detector collects photons from the measured object.

Optionally, the light source comprises a short-pulse light source; and the processor is further configured to: under different concentrations of the specific substance, by controlling the time when the short-pulse light source is turned on and the time when the short-pulse light source is turned off and controlling the time when the optical detector is turned on and the time when the optical detector is turned off by the time gate device, measure light intensity of photons of different optical lengths at the benchmark position; determine the specific optical length of the photons, the change rate of the light intensity of the photons of the specific optical length with the concentration of the specific substance in the measured object being less than or equal to the preset threshold; and measure the light intensity of the photons of the specific optical length at the benchmark position.

Optionally, the change rate of the light intensity of the photons of the specific optical length with the concentration of the specific substance in the measured object is substantially equal to zero.

Optionally, the benchmark position is a positional area; the concentration measurement device further comprises a light-converging device which is configured to converge photons in the positional area onto a probe of the optical detector.

Optionally, the benchmark position is a position where the change rate of the light intensity with the concentration of the specific substance in the measured object is the smallest among multiple positions that are at different distances from the light source in the measured object, and the measurement position is a position where the change rate of the light intensity with the concentration of the specific substance in the measured object is the largest among the multiple positions.

Optionally, the concentration measurement device further comprises a time gate device; the processor is further configured to measure light intensity of photons of a specific optical length at the benchmark position by utilizing the time gate device.

Optionally, the benchmark position is a positional point or a positional area.

Optionally, the processor is further configured to: use light intensity of photons of all optical lengths measured at the benchmark position as the light intensity reference value; use the light intensity of the photons of the specific optical length measured at the benchmark position as a benchmark light intensity reference value; and correct the light intensity measurement value by using the benchmark light intensity reference value, the light intensity reference value and the light intensity measurement value.

Optionally, the measured object comprises blood; and/or the specific substance comprises glucose.

[Description of Reference Signs]

| | |
|---|---|
| 1- light source | 2- incident fiber |
| 3-fiber probe | 4-displacement device |
| 5-time gate device | 6-optical detector |
| 7-data collector | 8-data processor |
| 9-measurement position | 10-benchmark position |
| 11-condenser lens | 12-control part |
| 13-time gate control part | |

DETAILED DESCRIPTION OF EMBODIMENTS

In order to make objectives, technical solutions and advantages of the present disclosure clearer, the present disclosure will be further described in detail below in conjunction with specific embodiments and with reference to the accompanying drawings.

In process of proposing the present disclosure, the inventors have found that when an optical detection method is used to measure the concentration of a specific substance in the measured object, an optical signal received by an optical detector may be typically affected by background change. How to extract weak concentration information of the specific substance from complex background change is a problem that needs to be solved.

The present disclosure provides a method for correcting a light intensity measurement value. The method includes: emitting detection light into a measured object; determining a benchmark position, a change rate of light intensity measured at the benchmark position with a concentration of a specific substance in the measured object being less than or equal to a preset threshold; using the light intensity measured at the benchmark position as a light intensity reference value; measuring a light intensity measurement value at a measurement position, wherein a change rate of the light intensity measured at the measurement position with the concentration of the specific substance in the measured object is greater than the change rate of the light intensity measured at the benchmark position with the concentration of the specific substance in the measured object; and correcting the light intensity measurement value by using the light intensity reference value.

According to some embodiments of the present disclosure, the light intensity of specific photons measured at the benchmark position is used as the light intensity reference value, and the light intensity measured at the measurement position is used as the light intensity measurement value. The background change in the measurement process is reflected in the light intensity reference value. The light intensity measurement value contains both concentration information of the specific substance and the background change information. By using the light intensity reference value to correct the light intensity measurement value, an influence of the background change in the measurement result may be effectively removed, and an accuracy of the measurement result may be improved.

Figure 1:
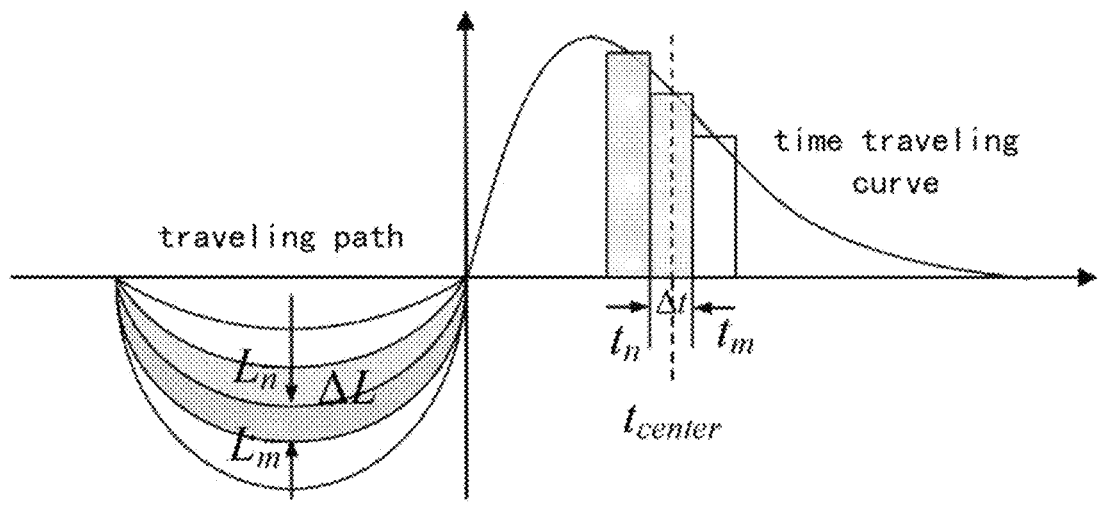
FIG. 1 is a schematic view showing the principle of the present disclosure.

FIG. 1 is a schematic view showing the principle of the present disclosure.

Specifically, FIG. 1 is a schematic view showing traveling paths, traveling time, and path lengths of photons in a homogeneous medium. Photons travel in random paths in the skin tissue, but a large number of photons may show statistical characteristics of their traveling paths. It is found through research that the traveling paths of diffusely-reflected photons in the homogeneous medium are mainly concentrated in a banana-shaped area from an incident point of a light source to an exit position of the photons, as shown in FIG. 1. The length of the photon's traveling path is the traveling optical length of the photon. Since only traveling time of the photon in the tissue may be detected in the actual detection, the traveling optical length may be converted into time by using $t=L/c$, wherein L is the photon traveling optical length, c is the speed at which the photon travels in the medium. For example, as shown in FIG. 1, the optical length $L_n$ corresponds to the traveling time $t_n$, the optical length $L_m$ corresponds to the traveling time $t_n$, an optical length difference $\Delta L$ corresponds to a traveling time difference $\Delta t$, and an intermediate value between $L_n$ and $L_m$ corresponds to an intermediate value $t_{center}$ between $t_n$ and $t_m$. In this way, photons of different optical lengths may be distinguished by the traveling time of photons. The diffusely-reflected photons of different optical lengths (i.e., different traveling time) collected by an optical detector probe are distinguished by a time gate device. Sensitivities of the photons, which reach the probe and undergo different traveling optical lengths, to concentration change of the specific substance is analyzed. The light intensity of the photons with low sensitivity to the concentration change of the specific substance (for example, the sensitivity is equal to 0) is measured and used as the light intensity reference value. The light intensity reference value is used to correct the light intensity measurement value. For example, a benchmark light intensity reference value in a benchmark state is obtained. The benchmark light intensity reference value, the light intensity reference value, and the light intensity measurement value are used to correct the light intensity measurement value, so that the measurement value is closer to the true value, thereby reducing measurement error. For example, the benchmark light intensity reference value is $I_0$, the light intensity reference value is $I_1$, and the light intensity measurement value is $I_2$, and the corrected light intensity measurement value is $I_2*I_0/I_1$.

According to the embodiments of the present disclosure, before and after the concentration of the specific substance in the measured object is changed, the light intensity may be measured at multiple positions which are at different distances from the light source. One of the multiple positions, where the change rate of the light intensity with the concentration of the specific substance is the smallest, may be used as the benchmark position, and one of the multiple positions, where the change rate of the light intensity with the concentration of the specific substance is the largest, may be used as the measurement position. When the detection light emitted by the light source enters the measured object, the change rate of the light intensity measured at different positions of the measured object varies with the concentration of the specific substance. One of the multiple positions, where the change rate of the light intensity with the concentration of the specific substance is the smallest, may be used as the benchmark position. According to the embodiments of the present disclosure, a position, where the change rate of the light intensity with the concentration of the specific substance is equal to zero, may be used as the benchmark position.

Further, a sensitivity of the light intensity of photons measured at the benchmark position to the concentration change of the specific substance is lower than a preset threshold, and the light intensity of photons may be used as the light intensity reference value. According to the embodiments of the present disclosure, the preset threshold may be set according to actual needs, for example, it may be set to a value very close to zero, or set to zero. For example, under different concentrations of the specific substance, by controlling both the time when a short-pulse light source is turned on and turned off and the time when an optical detector is turned on and turned off, the light intensity of photons of different optical lengths (i.e., different traveling time) may be measured at the benchmark position, so as to determine the specific optical length of the photons, the sensitivity of which to the concentration change of the specific substance is less than or equal to the preset threshold. In actual measurement, the light intensity of the photons of the specific optical length measured at the benchmark position is used as the light intensity reference value.

Compared with collecting photons of all traveling optical lengths when detecting at a certain position, the fixed optical length detection only extracts photons of a certain traveling optical length, thereby eliminating other irrelevant light. Although the light intensity becomes weak, a dynamic detection range of useful signal may be increased by a larger magnification to facilitate the extraction of the useful signal.

According to the embodiments of the present disclosure, the benchmark position is a positional point or a positional area.

When the benchmark position is a positional point, under ideal conditions (infinitely-thin light source is incident vertically and all diffusely-reflected photons are collected at the measurement position), when a source-detector separation (abbreviated as SDS or S-D) satisfies SDS=ρ, according to the traveling optical length L=ct, wherein c is a traveling speed of photons in the medium, t is a traveling time, and the traveling optical length distribution function of diffuse-reflection light energy $R_f$ at the probe may be obtained as:

$$I_r(\rho, L) = I_0 \left(\frac{4\pi L}{3(1-g)\mu_s}\right)^{-\frac{3}{2}} \exp\left(-\frac{3(1-g)\mu_s \rho^2}{4L}\right) \exp(-\mu_a L);$$

wherein ρ is the source-detector separation, L is the optical length, $I_0$ is the incident light energy, $\mu_a$ is the absorption coefficient of the medium, $\mu_s$ is the scattering coefficient of the medium, and g is the anisotropy coefficient of the medium.

Based on the traveling optical length distribution function of the diffuse-reflection light energy $R_f$ at the probe, it can be deduced that the detection sensitivity of the photons of the specific optical length at the benchmark position is equal to 0, that is, the light intensity of the photons of the specific optical length measured at the benchmark position is used as the light intensity reference value. The derivation process may be performed as follows.

As optical parameters of the medium change, according to research results of the inventors of the present disclosure on a change rule of the optical parameters with glucose concentration, the detection sensitivity of the photons which have a traveling optical length of L is obtained:

$$s(L) = \frac{dI_r(\rho, L)}{dC_g}\bigg|_{\rho=const} = \frac{\partial I_r}{\partial \mu_a} \cdot \frac{d\mu_a}{dC_g} + \frac{\partial I_r}{\partial \mu_s} \cdot \frac{d\mu_s}{dC_g} + \frac{\partial I_r}{\partial g} \cdot \frac{dg}{dC_g};$$

wherein ρ is SDS, $C_g$ is the glucose concentration, and ρ=const means ρ is a fixed value.

Through calculation, it may be obtained as follows:

$$s(L) = \frac{dI_r(\rho_n, L_{\rho n})}{dC_g}\bigg|_{L=const} = \left(\frac{3}{2\pi L}\right)^{\frac{3}{2}} \cdot \sqrt{\mu'_s} \cdot$$

$$\exp\left(-\mu_a L - \frac{3\mu'_s \rho^2}{2L}\right) \cdot \left[(-K\mu_s - 2W(\lambda)\mu'_{s0}) \cdot \left(\frac{3}{2} - \frac{3\mu'_s \rho^2}{2L}\right) - G\mu'_s L\right];$$

Wherein $\rho_n$ represents any SDS, $\mu_a=\mu_{a0}+(\varepsilon_g-6.1494\varepsilon_w)C_g$, $K=8.5\times10^{-5}$, $\mu_s=\mu_{s0}-2W(\lambda)\mu_{s0}C_g$, $g=g_0+8.5\times10^{-5}C_g$, $G=\varepsilon_g-k_w\varepsilon_w$, $\mu'_s=(1-g)\mu_s$, $\varepsilon_g$ is the molar absorption coefficient of glucose, $\varepsilon_w$ is the molar absorption coefficient of water, $W(\lambda)$ is the change factor of the scattering coefficient at different wavelengths.

Figure 2:
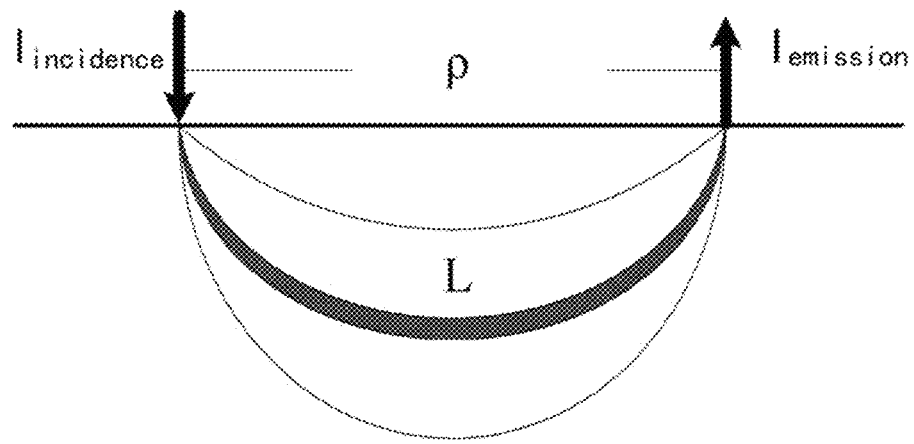
FIG. 2 shows a schematic view of the measurement method when a benchmark position is a positional point.

FIG. 2 shows a schematic view of the measurement method when the benchmark position is a positional point.

As shown in FIG. 2, ρ is the distance between the light source and the benchmark position. $I_{incidence}$ is the detection light emitted by the light source and incident on the measured object, $I_{emission}$ is the emitted light at the benchmark position, and the optical detector probe is disposed at the benchmark position to detect the emitted light. At the benchmark position, the sensitivity of the total emitted light of different traveling optical lengths to the concentration change of the specific substance is equal to 0, and there are photons of a special optical length L at the benchmark position, the sensitivity of the photons of a special optical length L to the concentration change of the specific substance is also equal to 0. Only the light intensity of the photons of the optical length L detected at the benchmark position are extracted as the light intensity reference value by the time gate method, thereby improving the accuracy of the detected light intensity.

Figure 3:
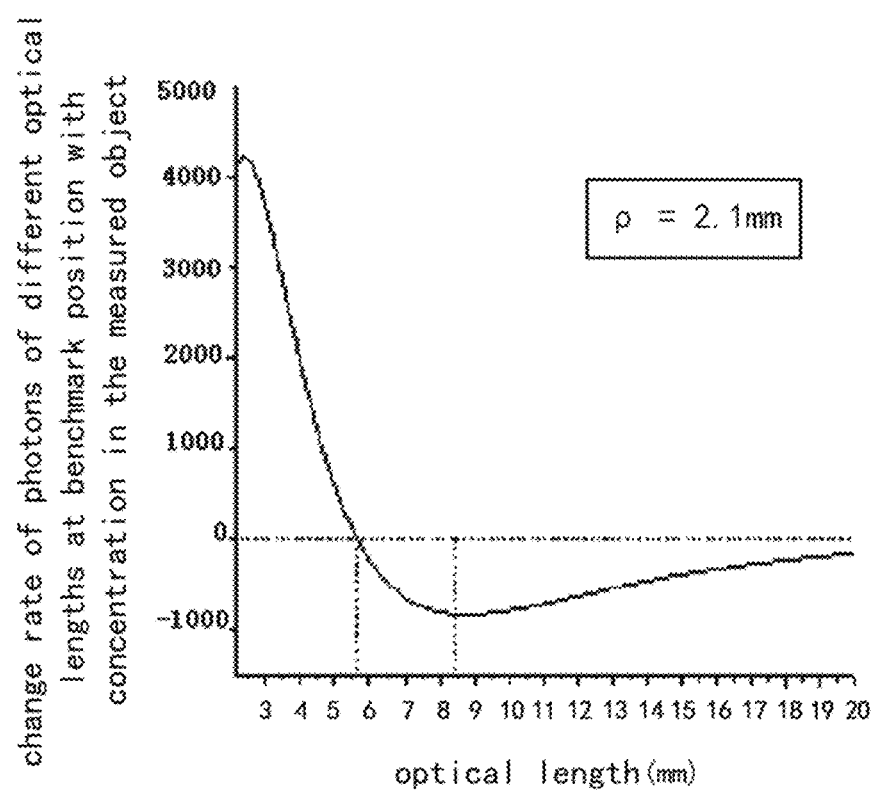
FIG. 3 shows a schematic view of a change rate of light intensity of photons of different optical lengths at the benchmark position with concentration of specific substance in a measured object.
Figure 4:
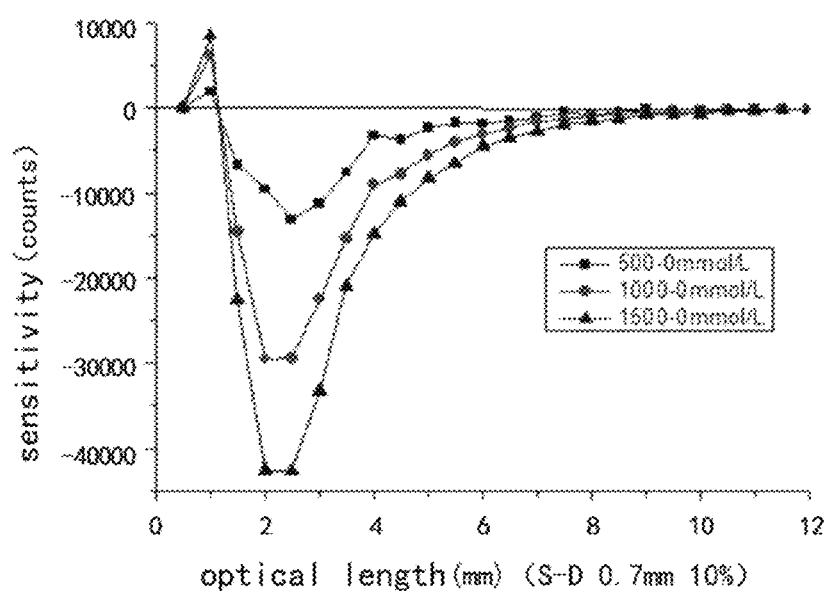
FIG. 4 shows a travelling optical length sensitivity distribution of 10% intralipid-glucose solution at a source-detector separation of 0.7 mm.
Figure 5:
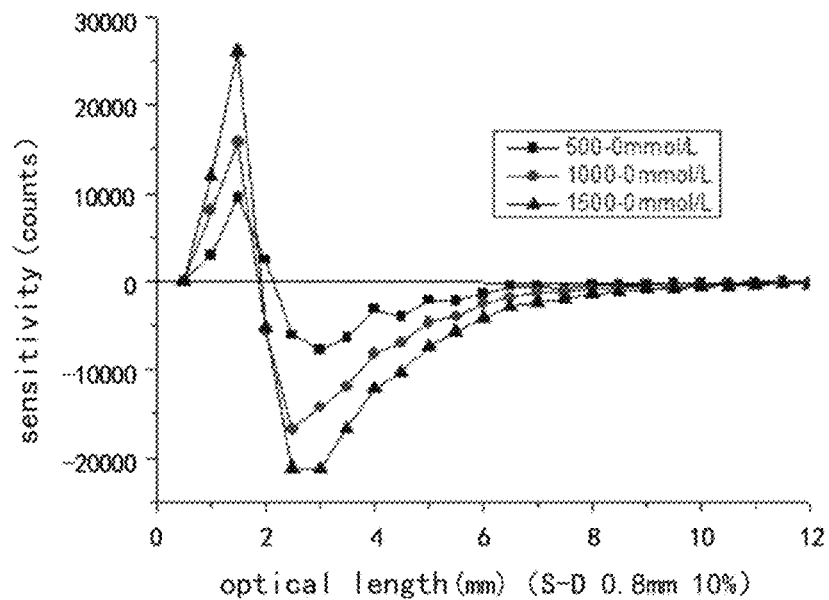
FIG. 5 shows a travelling optical length sensitivity distribution of 10% intralipid-glucose solution at a source-detector separation of 0.8 mm.
Figure 6:
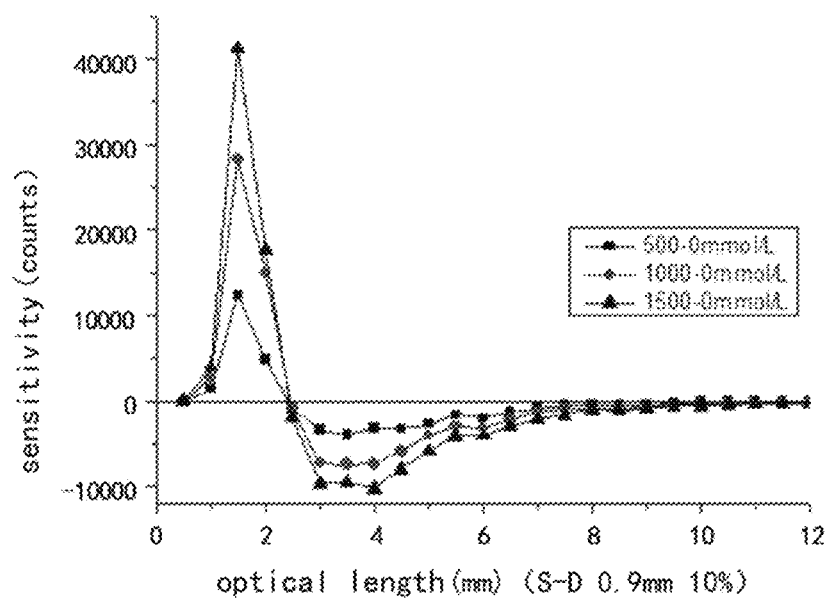
FIG. 6 shows a travelling optical length sensitivity distribution of 10% intralipid-glucose solution at a source-detector separation of 0.9 mm.
Figure 7:
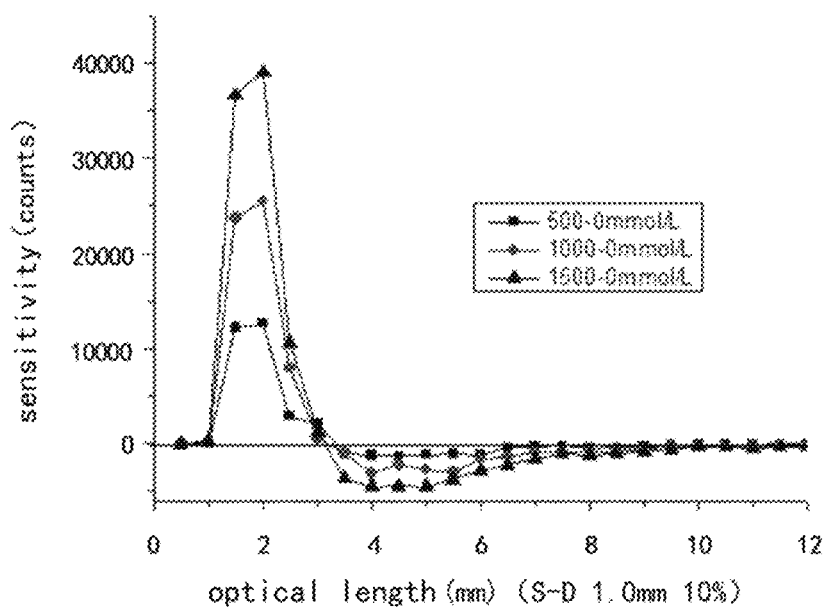
FIG. 7 shows a travelling optical length sensitivity distribution of 10% intralipid-glucose solution at a source-detector separation of 1.0 mm.
Figure 8:
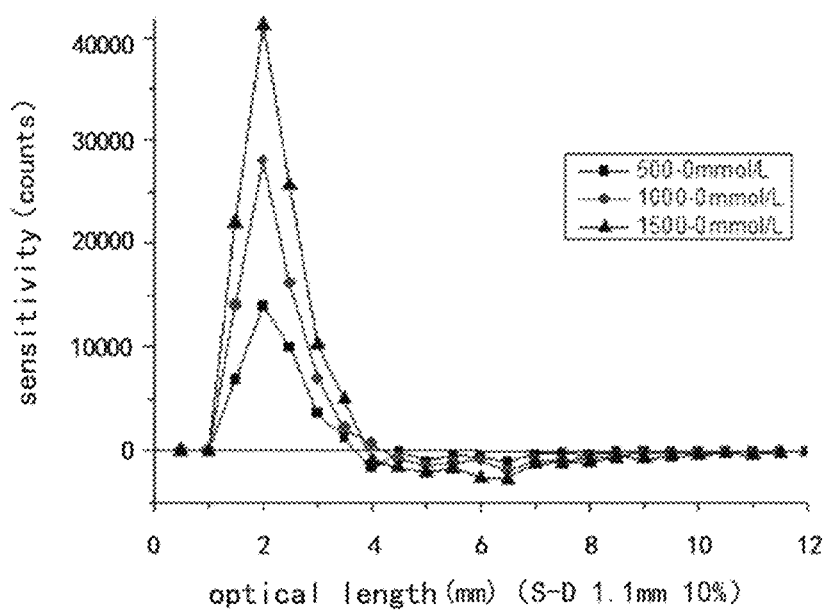
FIG. 8 shows a travelling optical length sensitivity distribution of 10% intralipid-glucose solution at a source-detector separation of 1.1 mm.
Figure 9:
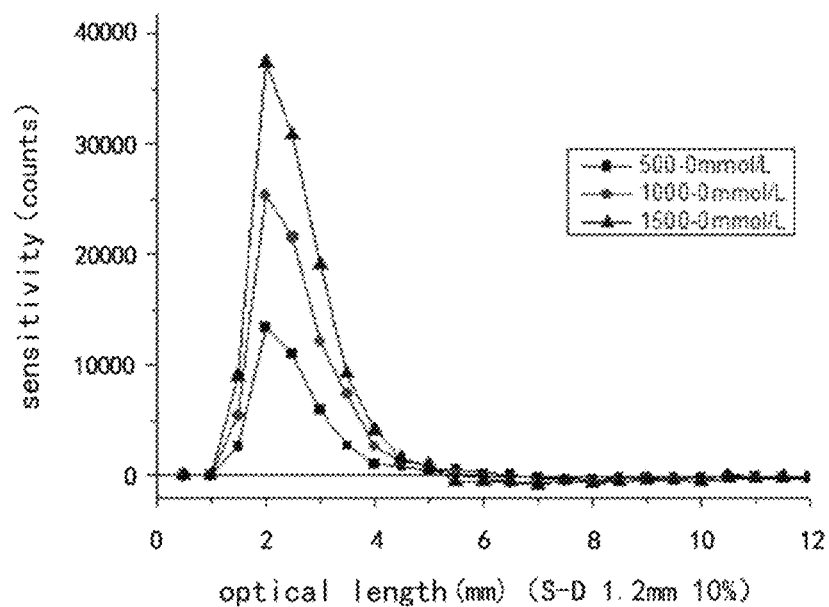
FIG. 9 shows a travelling optical length sensitivity distribution of 10% intralipid-glucose solution at a source-detector separation of 1.2 mm.
Figure 10:
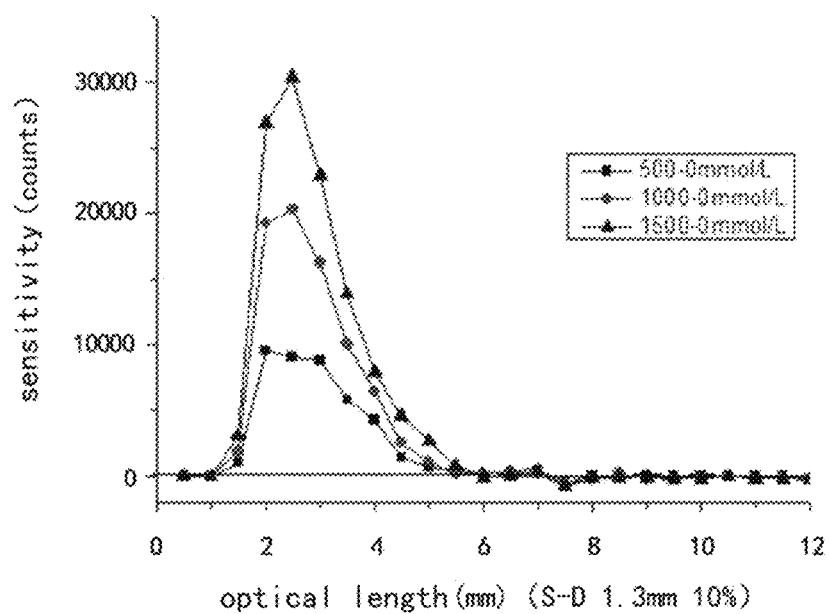
FIG. 10 shows a travelling optical length sensitivity distribution of 10% intralipid-glucose solution at a source-detector separation of 1.3 mm.

FIG. 3 shows a schematic view of the change rate of the light intensity of photons of different optical lengths at the benchmark position with the concentration of the specific substance in the measured object. It should be noted that, in FIG. 3 to FIG. 10 and FIG. 12, the ordinate represents the number of the photons, that is, a change rate of the number of the photons represents the change rate of the photons with the concentration of the specific substance in the measured object. For example, in FIG. 3 to FIG. 10 and FIG. 12, the number of the photons which is larger than zero expresses that a change of the number of the photons is positively related to a change of the concentration of the specific substance in the measured object, and the number of the photons which is smaller than zero expresses that a change of the number of the photons is negatively related to the change of the concentration of the specific substance in the measured object.

As shown in FIG. 3, at the benchmark position of ρ=2.1 mm, the change rate of the light intensity of the photons of an optical length of about 5.6 mm with the concentration of the specific substance in the measured object is equal to 0, that is, the sensitivity of the photons to the concentration change of the specific substance is equal to 0. Therefore, the light intensity of the photons of the optical length may be measured as the light intensity reference value.

FIG. 4 to FIG. 10 show the detection sensitivity distributions of 10% intralipid-glucose solution at different source-detector separations. As shown in FIG. 4~FIG. 10, a simulation is performed as for the 10% intralipid-glucose solution under the light source of 1200 nm. The traveling optical length sensitivity distributions are simulated when the source-detector separation is in the range of 0.7~1.3 mm. The abscissa is the optical length, and the ordinate is the sensitivity. It can be seen from the figures that at a certain source-detector separation, there is a certain optical length, at which the sensitivity to the concentration change of glucose is equal to 0.

According to the embodiments of the present disclosure, the benchmark position may also be a positional area, for example, the positional area may be a circular area which has a center as the light source and a radius of a preset distance, or the positional area may be a circular-ring area which has a center as the light source and a radius of a first preset distance and a second preset distance. The following derivation aims to prove that when the benchmark position is an area, there is also an optical length in which the sensitivity to the concentration change of glucose is equal to 0.

Figure 11:
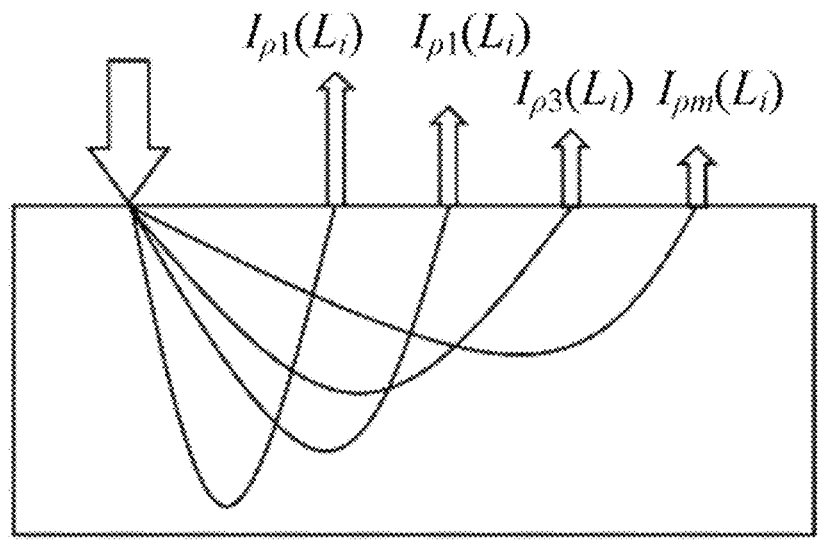
FIG. 11 is a schematic view showing all diffusely-reflected photons which are emitted from an entire circular area with a light source as the center and a detection radius as the radius and have a traveling optical length of $L_i$.

FIG. 11 is a schematic view showing all diffusely-reflected photons which are emitted from an entire circular area with the light source as the center and the detection radius as the radius and have a traveling optical length of $L_i$.

As shown in FIG. 11, the total number of photons picked up in each traveling optical length may be expressed as $\Sigma_{m=1}^{x/\Delta x} I_{\rho_m}(L_i)$:

$$\Sigma_{m=1}^{x/\Delta x} I_{\rho_m}(L_i) = I_{\rho_1}(L_i) + I_{\rho_2}(L_i) + I_{\rho_3}(L_i) + \ldots I_{\rho_m}(L_i)$$
$$(i=1,2,\ldots,n),$$

wherein $I_{\rho_m}(L_i)$ represents the number of photons of the optical length of $L_i$ when the source-detector separation is $\rho_m$.

By integrating the source-detector separations, the sum of the number of photons corresponding to certain traveling time emitted at all source-detector separations may be obtained as:

$$\int_0^x I_f(\rho, t)\Big|_{t=const} d\rho =$$

$$I_0 z_0 (4\pi Dc)^{-3/2} t^{-5/2} \exp(-\mu_a ct) \times \exp\left(-\frac{z_0^2}{4Dct}\right) \times \sqrt{\pi Dct} \; \text{Erf}\left(\frac{x}{2\sqrt{Dct}}\right)$$

wherein $I_f(\rho, t)$ represents the number of photons in certain traveling time at a certain source-detector separation, $\rho$ is the source-detector separation, t is the time, t=const means t is a fixed value, $$D = \frac{1}{3[\mu_a + (1-g)\mu_s]}, \; z_0 = \frac{1}{(1-g)\mu_s},$$

$I_0$ is the incident light energy, $\mu_a$ is the absorption coefficient of the medium, $\mu_s$ is the scattering coefficient of the medium, c is the speed of light, g is the anisotropy coefficient of the medium, $\mu'_s = (1-g)\mu_s$ When counting photons within $3\sigma$, there are:

$$\text{Erf}\left(\frac{x}{2\sqrt{Dct}}\right) = 1$$

then:

$$\int_0^x I_f(\rho, t)\Big|_{t=const} d\rho =$$

$$I_0 z_0 (4\pi Dc)^{-3/2} t^{-5/2} \exp(-\mu_a ct) \times \exp\left(-\frac{z_0^2}{4Dct}\right) \times \sqrt{\pi Dct}$$

according to L=ct, then:

$$\sum_0^x I_f(L)\Big|_{L=const} = \int_0^x I_f(\rho, t)\Big|_{t=const} d\rho =$$

$$z_0 (4\pi D)^{-3/2} L^{-5/2} \exp(-\mu_a L) \cdot \exp\left(-\frac{z_0^2}{4DL}\right) \cdot \sqrt{\pi Dct}$$

Taking the derivative of all diffusely-reflected photons under a certain traveling optical length to the glucose concentration, the sensitivity $s_l$ of all photons to the glucose concentration change under the traveling optical length may be calculated as:

$$s_l = \frac{\partial \sum_0^x I_f(L)}{\partial C_g}\Big|_{L=const} =$$

$$\frac{\partial \sum_0^x I_f(L)}{\partial \mu_a}\frac{d\mu_a}{dC_g} + \frac{\partial \sum_0^x I_f(L)}{\partial \mu_s}\frac{d\mu_s}{dC_g} + \frac{\partial \sum_0^x I_f(L)}{\partial g}\frac{dg}{dC_g};$$

wherein:

$$D = \frac{1}{3[\mu_a + (1-g)\mu_s]},$$

$$z_0 = \frac{1}{(1-g)\mu_s};$$

$$\frac{\partial \sum_0^x I_f(L)}{\partial \mu_a} = c\left(\frac{4\pi}{3}\right)^{-3/2} L^{-5/2} \sqrt{\frac{\pi L}{3}} \exp(-\mu_a L)\exp\left(-\frac{3z_0}{4}\right)\left(\frac{3z_0^2}{4L} - L\right);$$

$$\frac{\partial \sum_0^x I_f(L)}{\partial \mu_s} = c\left(\frac{4\pi}{3}\right)^{-3/2} L^{-5/2} \sqrt{\frac{\pi L}{3}} \exp(-\mu_a L)\exp\left(-\frac{3z_0}{4}\right)\frac{3z_0^2}{4L}(1-g);$$

$$\frac{\partial \sum_0^x I_f(L)}{\partial g} = -c\left(\frac{4\pi}{3}\right)^{-3/2} L^{-5/2} \sqrt{\frac{\pi L}{3}} \exp(-\mu_a L)\exp\left(-\frac{3z_0}{4}\right)\frac{3z_0^2}{4L}\mu_s$$

According to the influence of glucose concentration on optical parameters:

$$\frac{d\mu_s(\lambda)}{dC_g} = -2w(\lambda) \cdot \mu_{s0};$$

$$\frac{d\mu_a(\lambda)}{dC_g} = \varepsilon_g(\lambda) - 6.1494 \cdot \varepsilon_w(\lambda);$$

$$\frac{dg(\lambda)}{dC_g} = 8.45 \times 10^{-6};$$

it may be obtained that:

$$s_l = c \left(\frac{4\pi}{3}\right)^{-3/2} L^{-5/2} \sqrt{\frac{\pi L}{3}} \exp(-\mu_a L)$$

$$\exp\left(-\frac{3z_0}{4}\right) \cdot \left\{ \left(\frac{3z_0^2}{4L} - L\right)[\varepsilon_g(\lambda) - 6.1494\varepsilon_w(\lambda)] - \right.$$

$$\left. \frac{1.5(1-g)z_0^2 w(\lambda)\mu_{S0} - 6.3 \times 10^{-6} \mu_s z_0^2}{L} \right\}$$

Monte Carlo simulation may be used to calculate the traveling of photons in glucose solutions of 0 mg/dL, 500 mg/dL, 1000 mg/dL, and 1500 mg/dL prepared from 10% intralipid solution under 1280 nm light source. The sum of the number of diffusely-reflected photons under different traveling lengths is obtained. In order to count all the diffusely-reflected photons, the selected detection radius is 10 mm, the traveling optical length range is 0.5 mm, and the number of light source photons is $10^9$.

Figure 12:
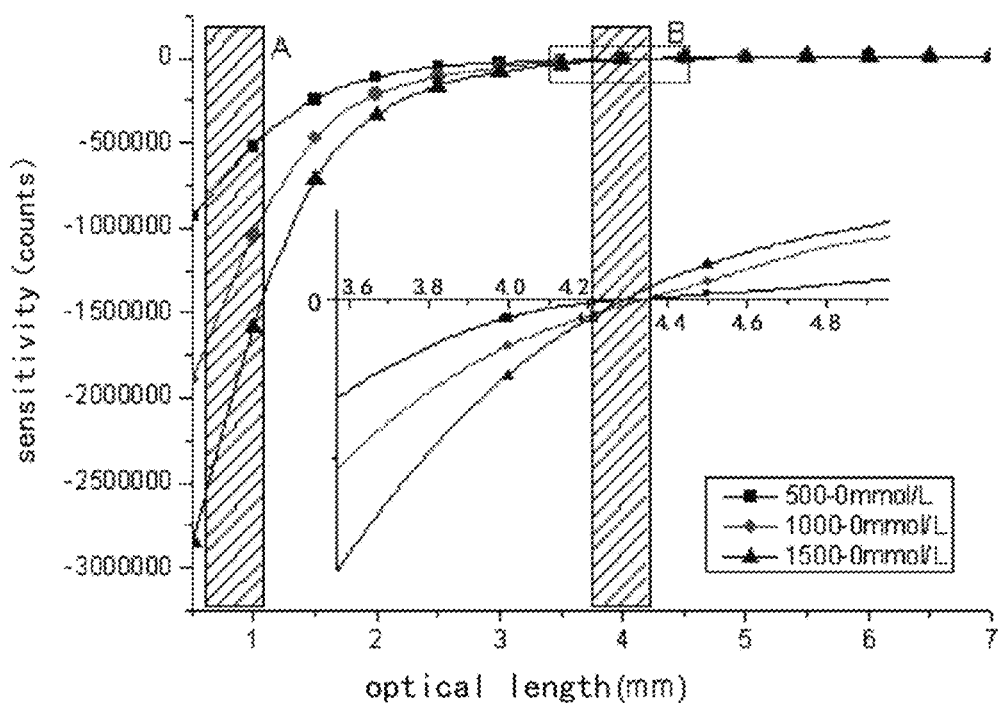
FIG. 12 is a graph showing a change of the total number of photons of the same traveling optical length within a radius of 10 mm from the light source on a surface of the 10% intralipid-glucose solution with the glucose concentration.

FIG. 12 is a graph showing a change of the sum of the number of photons of the same traveling optical length within a radius of 10 mm from the light source on the surface of the 10% intralipid-glucose solution with the glucose concentration. In FIG. 12, "A" and "B" represent two regular areas filled with oblique lines, respectively, and a curved-line diagram including values such as 3.6, 3.8, 4.0 in the horizontal ordinate is an enlarged view at the area "B".

As shown in FIG. 12, in the case of the 1280 nm light source, when the glucose concentration changes by 10%, the difference between the sum of the number of photons and the number of photons obtained in the case of 0mg/dL intralipid-glucose solution is calculated, wherein the sum of the number of photons are as for different traveling optical lengths emitted from a region within a radius of 10 mm from the light source on the surface of the intralipid-glucose solution medium. It can be seen that there is an intersection point at the position where the traveling optical length is 4.3 mm. On the left side of the intersection point, the number of diffusely-reflected photons is negatively correlated with the glucose concentration change, and on the right side of the intersection point, the number of diffusely-reflected photons is positively correlated with the glucose concentration change. The total number of diffusely-reflected photons of a traveling optical length of 4.3 mm within a radius of 10 mm from the light source is approximately independent of the glucose concentration change. It can be seen that the benchmark position may be a positional area from the light source, in this positional area, there is an optical length with a sensitivity of 0, that is, 4.3 mm.

Figure 13:
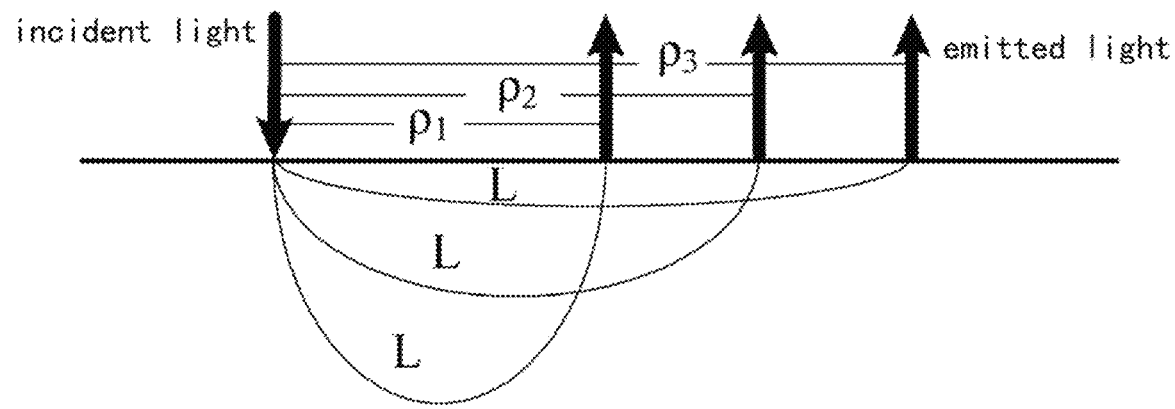
FIG. 13 is a schematic view showing the principle of a measurement method when the benchmark position is a positional area.

FIG. 13 is a schematic view showing the principle of the measurement method when the benchmark position is the positional area.

As shown in FIG. 13, when the source-detector separations are ρ1, ρ2, and ρ3, there are special optical lengths L in which the sensitivity to the concentration change of the measured object is equal to 0. All photons of the optical length of L within a certain source-detector separation range are extracted by the time gate method, thereby increasing the detected light intensity, and improving the signal-to-noise ratio and the detection accuracy. For example, the benchmark position may be set as an area including three positions with distances of ρ1, ρ2, and ρ3 to the light source, or the benchmark position may be set as a circle with the light source as the center and any distance of ρ1, ρ2, or ρ3 as the radius, or the benchmark position may be set as a circular ring with the light source as the center, ρ1 as the inner radius, and ρ3 as the outer radius.

Compared with the situation where the positional point is used as the benchmark position, the positional area is used as the benchmark position, the requirement for the accuracy of the probe positioning is low. Small deviations will not cause excessive loss of effectiveness when using the light intensity reference value to correct the light intensity measurement value, so as to avoid introducing measurement errors. By extending the benchmark position into a band, the applicability of the method of the present disclosure may be improved.

Figure 14:
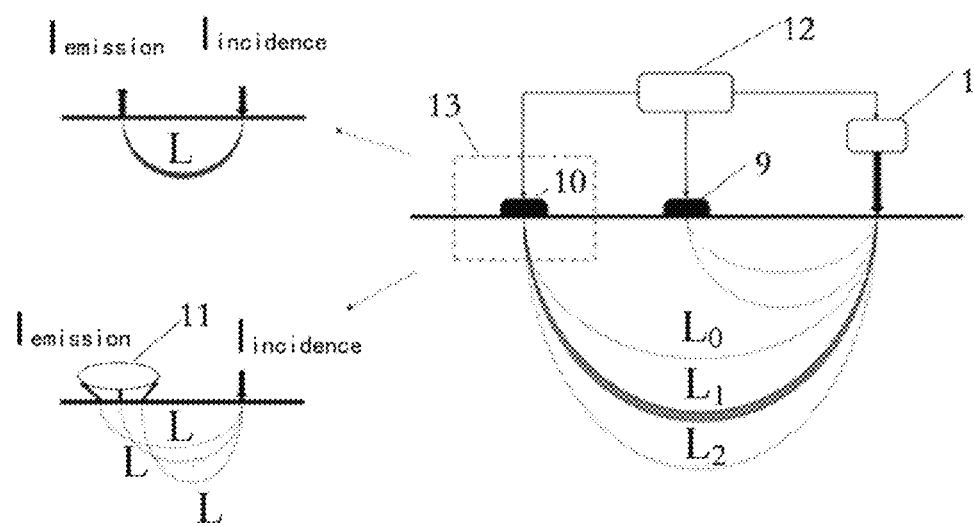
FIG. 14 is a schematic view of a concentration measurement device in which a reference value is measured at a time gate fixed optical length.

FIG. 14 is a schematic view of a concentration measurement device in which a reference concentration is measured at a time gate fixed optical length.

As shown in FIG. 14, the concentration measurement device includes a light source 1, a control part 12, and a time gate control part 13. The control part 12 controls the time when the light source is turned on and the time when the light source is turned off, and the time gate control part 13 controls the time when the optical detector is turned on and the time when the optical detector is turned off, so that the optical detector only measures the intensity of the photons of the specific optical length as the light intensity reference value. The control part 12 corrects the light intensity measurement value obtained at the measurement position 9 with the light intensity reference value, and the concentration of the specific substance in the measured object may be obtained based on the corrected light intensity measurement value.

As shown in FIG. 14, when the benchmark position is a positional point, the probe of the optical detector is disposed at the positional point, and the photons of the specific optical length L is collected by the optical fiber probe. When the benchmark position is a positional area, the photons of the specific optical length L in the positional area is converged to the probe by using a light-converging method. For example, a lens may be embedded on a surface of the light probe to converge the light, or a ring-shaped condenser lens 11 (a cross-section of the ring-shaped condenser lens 11 is shown in FIG. 14) is used to converge the light onto the probe.

As for different measured objects, traveling optical lengths at which the sensitivity is equal to 0 may be different. The time when the light source is turned on and the time when the light source is turned off may be adjusted, and the time when the optical detector is turned on and the time when the optical detector is turned off may be also adjusted, so as to adjust the traveling time t of the received photons, thereby obtaining the traveling optical lengths at which the sensitivity is equal to 0 as for different measured objects. For example, if the photons of the specific optical length range of $l_0+\Delta l$ are collected, the time when the light source is turned on and the time when the light source is turned off may be adjusted, and the time when the optical detector is turned on and the time when the optical detector is turned off may be also adjusted, so as to only collect the photons with the traveling time of $l_0/c \sim (l_0+\Delta l)/c$ in the measured object, wherein c is the traveling speed of light in the measured object, and $\Delta l/c$ is the opening width. In this way, the method may be adapted to the measurement needs of different individuals without manually or mechanically adjusting the distance of the benchmark position or designing a variety of fiber optic probes.

Figure 15:
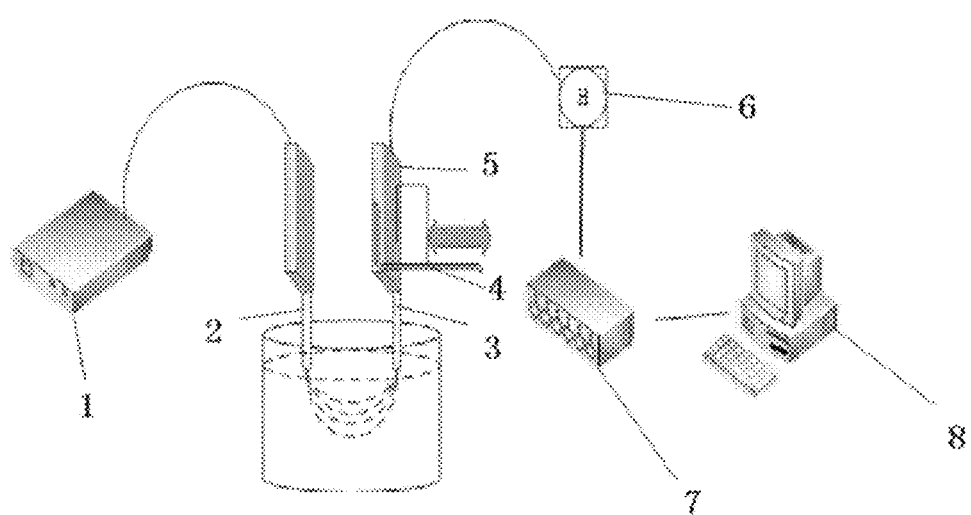
FIG. 15 is a schematic view of a concentration detection device according to embodiments of the present disclosure.

FIG. 15 is a schematic view of a concentration detection device according to the embodiments of the present disclosure.

As shown in FIG. 15, the concentration measurement device includes a light source 1, an incident optical fiber 2, an optical fiber probe 3, a displacement device 4, a time gate device 5, an optical detector 6, a data collector 7 and a data processor 8. Wherein, detection light is emitted from the light source 1 and enters the measured object through the incident optical fiber 2, and the optical detector 6 collects photons from the measured object through the optical fiber probe 3. The displacement device 4 controls the optical fiber probe to move to the benchmark position or the measurement position. The optical detector 6 measures the light intensity measurement value at the measurement position. By controlling the time when the light source is turned on and the time when the light source is turned off, and by controlling the time when the optical detector 6 is turned on and the time when the optical detector 6 is turned off by the time gate device 5, the optical detector 6 measures the light intensity of the photons at the benchmark position as the light intensity reference value, wherein the sensitivity of the light intensity of the photons to the concentration change of the specific substance in the measured object is less than or equal to the preset threshold. The measurement position and the benchmark position are determined according to the change rates measured at a plurality of positions with different distances from the light source in the measured object, wherein the change rates are represented by change rates of the light intensity with the concentration of the specific substance in the measured object. The benchmark position may be a position where the change rate of the light intensity with the concentration of the specific substance is the smallest among the plurality of positions, and the measurement position may be a position where the change rate of the light intensity with the concentration of the specific substance is the largest among the plurality of positions. Alternatively, the benchmark position may be a position where the change rate of the light intensity with the concentration of the specific substance is zero. The data processor 8 uses the light intensity reference value to correct the light intensity measurement value, for example, it may obtain a benchmark light intensity reference value in a benchmark state, and use the benchmark light intensity reference value, the light intensity reference value, and the light intensity measurement value to correct the light intensity measurement value. According to experiments or numerical simulations, the corresponding relationship between the light intensity measurement value and the concentration of the specific substance may be obtained. Based on the relationship, the data processor 8 may use the corrected light intensity measurement value to obtain the concentration of the specific substance in the measured object.

According to the embodiments of the present disclosure, the light source 1 includes a short pulse light source. By controlling the time when the short pulse light source is turned on and the time when the short pulse light source is turned off, and by controlling the time when the optical detector 6 is turned on and the time when the optical detector 6 is turned off by the time gate device 5, the optical detector 6 collects the photons, wherein the sensitivity of the photons to the concentration change of the specific substance is less than or equal to a preset threshold, for example, the sensitivity of the photons to the concentration change of the specific substance is equal to 0.

According to the embodiments of the present disclosure, the benchmark position may be a positional point, a positional area, or a circular ring centered on the light source, the measured object may include blood, and the specific substance may be glucose.

According to the embodiments of the present disclosure, when the benchmark position is a positional area, the concentration measurement device may further include a light-converging device for converging the photons in the positional area onto the probe of the optical detector. The light-converging device may be a converging lens.

In the embodiments of the present disclosure, the light intensity of photons that are insensitive to the concentration of the specific substance and the light intensity of photons that are more sensitive to the concentration of the specific substance are picked up by a time gate method to be used as the light intensity reference value and the light intensity measurement value, respectively. The light intensity measurement value is corrected by using the light intensity reference value, thereby reducing the interference of external factors on the measurement value, and reducing the system error.

Hereinafter, in conjunction with specific examples, effects of the method for correcting the light intensity measurement value and the concentration measurement device in which the reference concentration is measured at a time gate fixed optical length according to the present disclosure will be described in further detail.

Example 1 Simulation Experiment of a Measurement Method in which a Reference Value is Measured at a Single-Point Fixed Optical Length Simulation parameters: MCMLGO simulation is used for the medium of 2% intralipid-glucose solution. The glucose concentration is 0mg/dL, 500 mg/dL, 1000 mg/dL and 1500 mg/dL. In the case of 1200 nm light source, the number of photons emitted by the light source is $10^9$.

Varied parameters: light source energy fluctuation ±5% and ±10%.

Measurement value: at the measurement position, the sum of photons of all traveling optical lengths is selected as the light intensity measurement value.

Reference value: the number of photons which are emitted from the benchmark position and have the traveling optical length of the benchmark traveling optical length is used as the reference value. According to theoretical analysis, for the 2% intralipid-glucose solution, the benchmark traveling optical length of the photons emitted from the benchmark position is 4.0±0.2 mm, and the total number of the photons within the optical length range is used as the reference value.

When the light source power changes by ±5% and ±10%, the change coefficient of the total number of photons at the benchmark traveling optical length $\eta=I_1/I_0$, wherein $I_0$ is the number of photons at the benchmark traveling optical length before the light source power changes, and $I_1$ is the number of photons at the benchmark traveling optical length after the light source power changes. The measurement value $I_2$ which is affected by the fluctuation of the light source energy is corrected with $\eta$, and the corrected photon number is $I_2/\eta$. It can be seen from Table 1 below that the corrected light intensity value is very close to the standard value.

TABLE 1

Comparison of experimental results

| fluctuation rate of light source energy | fluctuation rate of detection light energy before correction | fluctuation rate of detection light energy after correction |
|---|---|---|
| −10% | 9.8% | 1.1% |
| −5% | 4.4% | 1.7% |
| 5% | 5.4% | 0.39% |
| 10% | 10% | 0.35% |

Taking the 1000 mg/dl intralipid-glucose solution as an example, the change in the measurement value caused by the fluctuation of the light source energy before the correction and the change in the measurement value after the correction may be calculated. It can be seen that the fluctuation of the detected light energy is significantly reduced after the measurement value is corrected by the fluctuation coefficient obtained by the fluctuation of the total number of the photons of the benchmark traveling optical length.

Example 2 Simulation Experiment Results of a Measurement Method in which a Reference Value is Measured at a Multi-Point Fixed Optical Length Simulation parameters: MCMLGO is used to simulate the traveling of photons in the tissue and the distribution of emission on the surface of the medium. The 2% intralipid-glucose solution is used as the medium, and the glucose concentration is 0mg/dL, 500 mg/dL, 1000 mg/dL and 1500 mg/dL. In the case of 1200 nm light source, the number of photons emitted from the light source is $10^9$.

Varied parameters: light source energy fluctuates within ±5% and ±10%, respectively.

Measurement value: the total number of photons which have a middle traveling optical length of 1.25 mm and a traveling optical length range of 1.25±0.25 mm is used as the measurement value.

Reference value: the total number of photons, which are emitted from the detection radius and have the traveling optical length that is equal to the benchmark traveling optical length, is used as the reference value. According to theoretical analysis, for a 2% intralipid-glucose solution, the benchmark traveling optical length is in a range of 1.25±0.25 mm, and the total number of photons in the optical length range is used as the reference value.

When the light source power changes by ±5% and ±10%, the measurement value which is affected by the fluctuation of the light source energy may be corrected by the change coefficient of the total number of photons at the benchmark traveling optical length. It can be seen from Table 2 below that the corrected light intensity value is very close to the standard value.

TABLE 2

Comparison of experimental results

| fluctuation rate of light source energy | fluctuation rate of detection light energy before correction | fluctuation rate of detection light energy after correction |
|---|---|---|
| −10% | 9.87% | 0.19% |
| −5% | 5.1% | 0.33% |
| 5% | 4.6% | 0.47% |
| 10% | 10.17% | 0.37% |

Taking the 1000 mg/dl intralipid-glucose solution as an example, the change in the measurement value caused by the fluctuation of the light source energy before the correction and the change in the measurement value after the correction may be calculated. It can be seen that the fluctuation of the detection light energy is significantly reduced after the measurement value is corrected by the fluctuation coefficient obtained by the fluctuation of the total number of the photons with the benchmark traveling optical length.

Therefore, in the method for correcting the light intensity measurement value and the concentration measurement device in which the reference value is measured at the time gate fixed optical length according to the present disclosure, the time gate detection method is applied to concentration measurement, and the time gate method is used to pick up the light intensity of photons that are insensitive to the concentration of the specific substance and the light intensity of photons that are more sensitive to the concentration of the specific substance as the measurement reference value and the measurement value, respectively. The reference value is used to correct the measurement value, and the background interference that is independent to the concentration of the measured object is deducted, so that the measurement value is closer to the true value, thereby reducing the system error.

In the specific embodiments described above, objectives, technical solutions and beneficial effects of the present disclosure are described in detail. It should be understood that the above descriptions are only specific embodiments of the present disclosure and are not intended to limit the present disclosure. Any modification, equivalent replacement, improvement and the like within the spirit and principle of the present disclosure shall be included in the protection scope of the present disclosure.

What is claimed is:

1. A method for correcting a light intensity measurement value, wherein the method comprises:
    emitting detection light into a measured object;
    determining a benchmark position, a change rate of light intensity measured at the benchmark position with a concentration of a specific substance in the measured object being less than or equal to a preset threshold;
    using the light intensity measured at the benchmark position as a light intensity reference value;
    utilizing a time gate device to control an optical detector to measure light intensity of photons of a specific optical length at the benchmark position;
    measuring a light intensity measurement value at a measurement position, wherein a change rate of the light intensity measured at the measurement position with the concentration of the specific substance in the measured object is greater than the change rate of the light intensity measured at the benchmark position with the concentration of the specific substance in the measured object; and
    correcting the light intensity measurement value by using the light intensity reference value,
    the step of utilizing the time gate device to control the optical detector to measure light intensity of photons of the specific optical length at the benchmark position comprises:
    under different concentrations of the specific substance, by controlling the time when a light source for emitting the detection light is turned on and the time when the light source is turned off and controlling the time when the optical detector is turned on and the time when the optical detector is turned off by the time gate device, measuring light intensity of photons of different optical lengths at the benchmark position;

determining the specific optical length of the photons the change rate of the light intensity of the photons of the specific optical length with the concentration of the specific substance in the measured object being less than or equal to the preset threshold; and measuring the light intensity of the photons of the specific optical length at the benchmark position.

2. The method according to claim 1, wherein, the step of using the light intensity measured at the benchmark position as the light intensity reference value comprises: using the light intensity of the photons of the specific optical length measured at the benchmark position as the light intensity reference value.

3. The method according to claim 1, wherein,
the change rate of the light intensity of the photons of the specific optical length with the concentration of the specific substance in the measured object is substantially equal to zero.

4. The method according to claim 1, wherein,
the benchmark position is a position where the change rate of the light intensity with the concentration of the specific substance in the measured object is the smallest among multiple positions that are at different distances from a light source in the measured object, and the measurement position is a position where the change rate of the light intensity with the concentration of the specific substance in the measured object is the largest among the multiple positions; and/or
the benchmark position is a position where the change rate of the light intensity with the concentration of the specific substance is equal to zero.

5. The method according to claim 1, wherein the benchmark position is a positional point or a positional area.

6. The method according to claim 5, wherein,
in response to that the benchmark position is the positional point, a probe of the optical detector is disposed at the positional point;
in response to that the benchmark position is the positional area, photons in the positional area are converged to the probe by using a light-converging method.

7. The method according to claim 5, wherein,
in response to that the benchmark position is the positional point, the photons of the specific optical length are collected at the positional point by a probe of the optical detector;
in response to that the benchmark position is the positional area, a lens is provided at the positional area to focus the photons in the positional area onto the probe.

8. The method according to claim 1, wherein the step of correcting the light intensity measurement value by using the light intensity reference value comprises:
using light intensity of photons of all optical lengths measured at the benchmark position as the light intensity reference value;
using the light intensity of the photons of the specific optical length measured at the benchmark position as a benchmark light intensity reference value; and
correcting the light intensity measurement value by using the benchmark light intensity reference value, the light intensity reference value and the light intensity measurement value.

9. A concentration measurement device, wherein the device comprises:
a light source configured to emit detection light into a measured object;

an optical detector configured to measure light intensity at at least one position in the measured object;
a processor which is in communication with the light source and the optical detector; and
a time gate device,
wherein the processor is configured to:
determine a benchmark position, a change rate of light intensity measured at the benchmark position with a concentration of a specific substance in the measured object being less than or equal to a preset threshold;
use the light intensity measured at the benchmark position as a light intensity reference value;
measure light intensity of photons of a specific optical length at the benchmark position by utilizing the time gate device;
measure a light intensity measurement value at a measurement position, wherein a change rate of the light intensity measured at the measurement position with the concentration of the specific substance in the measured object is greater than the change rate of the light intensity measured at the benchmark position with the concentration of the specific substance in the measured object; and
correct the light intensity measurement value by using the light intensity reference value,
wherein the light source comprises a short-pulse light source; and
the processor is further configured to:
under different concentrations of the specific substance, by controlling the time when the short-pulse light source is turned on and the time when the short-pulse light source is turned off and controlling the time when the optical detector is turned on and the time when the optical detector is turned off by the time gate device, measure light intensity of photons of different optical lengths at the benchmark position;
determine the specific optical length of the photons, the change rate of the light intensity of the photons of the specific optical length with the concentration of the specific substance in the measured object being less than or equal to the preset threshold; and
measure the light intensity of the photons of the specific optical length at the benchmark position.

10. The device according to claim 9, wherein, the device further comprises:
an incident optical fiber, through which the detection light emitted from the light source is transmitted into the measured object; and
an optical fiber probe, through which the optical detector collects photons from the measured object.

11. The device according to claim 9, wherein,
the change rate of the light intensity of the photons of the specific optical length with the concentration of the specific substance in the measured object is substantially equal to zero.

12. The device according to claim 9, wherein,
the benchmark position is a position where the change rate of the light intensity with the concentration of the specific substance in the measured object is the smallest among multiple positions that are at different distances from the light source in the measured object, and the measurement position is a position where the change rate of the light intensity with the concentration of the specific substance in the measured object is the largest among the multiple positions.

13. The device according to claim 9, wherein, the benchmark position is a positional point or a positional area.

14. The device according to claim 13, wherein,
the benchmark position is a positional area;
the concentration measurement device further comprises a light-converging device which is configured to converge photons in the positional area onto a probe of the optical detector.

15. The device according to claim 9, wherein, the processor is further configured to:
use light intensity of photons of all optical lengths measured at the benchmark position as the light intensity reference value;
use the light intensity of the photons of the specific optical length measured at the benchmark position as a benchmark light intensity reference value; and
correct the light intensity measurement value by using the benchmark light intensity reference value, the light intensity reference value and the light intensity measurement value.

16. The device according to claim 9, wherein the measured object comprises blood; and/or
the specific substance comprises glucose.

* * * * *